United States Patent
Odermatt et al.

(10) Patent No.: US 8,936,619 B2
(45) Date of Patent: Jan. 20, 2015

(54) SURGICAL SUTURE MATERIAL WITH BARBS CUT INTO IT IN THE UNDRAWN STATE

(75) Inventors: Erich Odermatt, Schaffhausen (CH); Ingo Berndt, Tuttlingen (DE); Silke König, Rottweil (DE); Erhard Müller, Stuttgart (DE); Sven Oberhoffner, Weinstadt-Endersbach (DE); Heinrich Planck, Nürtingen (DE)

(73) Assignees: Aesculap AG (DE); ITV Denkendorf Produktservice GmbH (DE)

( * ) Notice: Subject to any disclaimer, the term of this patent is extended or adjusted under 35 U.S.C. 154(b) by 929 days.

(21) Appl. No.: 13/128,047

(22) PCT Filed: Nov. 6, 2009

(86) PCT No.: PCT/EP2009/007950
§ 371 (c)(1),
(2), (4) Date: Aug. 3, 2011

(87) PCT Pub. No.: WO2010/052007
PCT Pub. Date: May 14, 2010

(65) Prior Publication Data
US 2011/0282384 A1    Nov. 17, 2011

(30) Foreign Application Priority Data
Nov. 6, 2008  (DE) .................. 10 2008 057 218

(51) Int. Cl.
*A61B 17/04* (2006.01)
*A61B 17/06* (2006.01)
*A61B 17/00* (2006.01)

(52) U.S. Cl.
CPC . *A61B 17/06166* (2013.01); *A61B 2017/00526* (2013.01); *A61B 2017/06176* (2013.01)
USPC ........................................... 606/228; 264/167

(58) Field of Classification Search
USPC .................. 606/219, 228–232, 222, 224, 225; 83/880, 861; 206/63.3; 428/357, 364; 264/145, 167, 281; 29/7.1–7.3
See application file for complete search history.

(56) References Cited

U.S. PATENT DOCUMENTS

| 3,123,077 A | 3/1964 | Alcamo |
| 2008/0221618 A1 | 9/2008 | Chen et al. |
| 2008/0255612 A1 | 10/2008 | Hunter |
| 2011/0093010 A1 | 4/2011 | Genova et al. |
| 2011/0166597 A1* | 7/2011 | Herrmann et al. ............ 606/228 |

FOREIGN PATENT DOCUMENTS

| DE | 602 19 181 | 1/2008 |
| EP | 1 559 266 B1 | 8/2007 |
| EP | 1 560 683 B1 | 8/2007 |
| EP | 1 555 946 B1 | 9/2007 |
| EP | 1 867 288 A1 | 12/2007 |
| GB | 1091282 A | 11/1967 |
| WO | 2009/105663 A2 | 8/2009 |

* cited by examiner

*Primary Examiner* — Dianne Dornbusch
*Assistant Examiner* — Robert Lynch
(74) *Attorney, Agent, or Firm* — DLA Piper LLP (US)

(57) ABSTRACT

A drawn surgical suture material includes an elongate main body and barbs for anchoring in biological tissues, wherein the barbs are formed by cuts made into the suture material in the undrawn state.

10 Claims, 5 Drawing Sheets

SURGICAL SUTURE MATERIAL WITH BARBS CUT INTO IT IN THE UNDRAWN STATE

RELATED APPLICATIONS

This is a §371 of International Application No. PCT/EP2009/007950, with an international filing date of Nov. 6, 2009 (WO 2010/052007 A2, published May 14, 2010), which is based on German Patent Application No. 10 2008 057 218.7, filed Nov. 6, 2008, the subject matter of which is incorporated by reference.

TECHNICAL FIELD

This disclosure relates to a drawn surgical suture material with an elongate main body and with barbs for anchoring in biological tissues, particularly in human and/or animal tissues, to a surgical kit, and to a method for producing the surgical suture material.

BACKGROUND

Thread-like suture materials are used as standard in surgery for closure of wounds. They are usually knotted to be securely fixed in the tissue. Care has to be taken to ensure that the wounds to be closed are sutured with an optimal force at the wound margins. If the wound margins are sutured too loosely and too irregularly, for example, there is in principle a risk of increased scar formation or dehiscence. By contrast, if the wound margins are sutured too strongly, there is a danger of the circulation of blood in the wound margins being restricted, which can result in necrotic changes in the surrounding tissue area.

In addition to the risk of possible complications, in particular further surgical interventions, there is therefore always a degree of risk of the wound repair, based on knotting of suture materials, leading to impaired healing and to unsatisfactory cosmetic results in the patients concerned. Another consideration is that several knots, in particular up to seven knots, often have to overlap to achieve a secure knot hold. This entails introducing a large amount of material into the area of the wound that is to be treated and can lead to increased foreign-body reactions, particularly in the case of resorbable suture material.

Suture materials which, in contrast to known or conventional threads, do not have to be knotted have long been known as "barbed sutures." Such knotless or self-fixing suture materials are usually composed of a monofilament thread which, along its longitudinal axis, has structures called 'barbs.' Corresponding suture materials are described, for example, in U.S. Pat. No. 3,123,077 A, EP 1 559 266 B1, EP 1 560 683 B1 and EP 1 555 946 B1. The barbs are formed on a thread such that the thread can be pulled through the tissue along the direction of the barbs without any great resistance and without tissue trauma. When a pull is exerted in the opposite direction, however, the barbs stand upright and anchor themselves, and therefore also the suture material, in the surrounding tissue area. This ensures that the suture material cannot be pulled back through the incision channel.

To produce the barbs, cuts are made into a drawn thread material. A problem here is that the thread material, because of its being drawn, has an already narrowed diameter, with the result that cutting into a thread material of this kind may cause problems in terms of mechanical load-bearing capacity if the thread is cut too deep. If the barbs are cut too deep into the suture material, even the slightest loads can lead to a tearing of the cuts and, consequently, to a destabilization of the suture material. In extreme cases, breaks may appear in the suture material.

It could therefore be helpful to make available a knotless or self-fixing suture material which avoids the disadvantages known from the prior art and in particular provides sufficient safety and load-bearing in wound closure. Moreover, it could be helpful to make available a corresponding method of production which has clear advantages over the conventional methods for production of knotless suture materials.

SUMMARY

We provide a drawn surgical suture material including an elongate main body and barbs for anchoring in biological tissues, wherein the barbs are formed by cuts made into the suture material in the undrawn state.

We also provide an undrawn surgical suture material including an elongate main body and barbs for anchoring in human and/or animal tissues.

We further provide a surgical kit including at least one surgical needle and the suture material.

We still further provide a method for producing the surgical suture material including a) cutting barbs into an undrawn suture material fiber, and b) thawing the suture material fiber to form the surgical suture material.

DETAILED DESCRIPTION

Figure 1A:
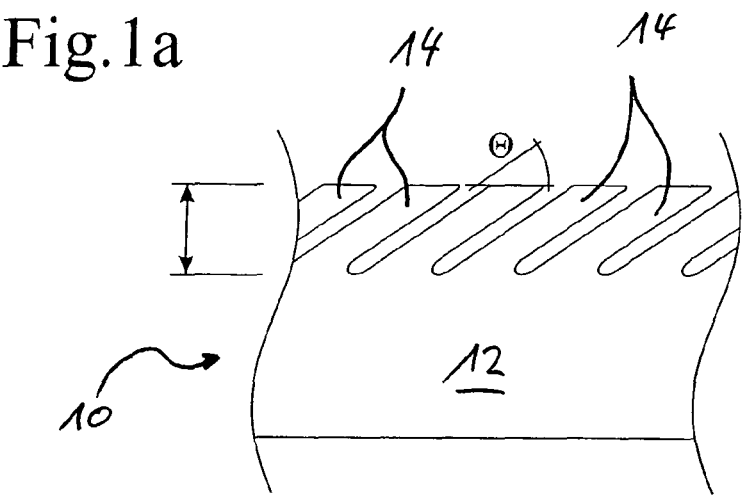
FIG. 1a shows a suture material fiber in the undrawn state, with cuts made in it.

The suture material is a drawn surgical suture material with an elongate main body and with barbs for anchoring in biological tissues, particularly in human and/or animal tissues, characterized in that the barbs are formed by cuts made into the suture material in the undrawn state.

We thus provide a suture material in which cuts are made in the undrawn state to form barbs and which is then drawn. In other words, a surgical suture material has a drawn elongate main body and barbs provided for anchoring in biological tissues, particularly in human and/or animal tissues. Depending on the cutting angle, the barbs can be present in a drawn form in parts, particularly in the area of emergence from the main body. By virtue of the fact that the elongate main body generally tapers when drawn, whereas the barbs substantially retain their original size and shape, completely new and variable barb geometries can be obtained. In particular, compared to the elongate main body, the barbs can have other mechanical properties, particularly with respect to hardness, flexibility, bendability and elasticity. Moreover, the properties of the barbs can be specifically adapted to the properties of the suture material. Surprisingly, it has also been found that a suture material of this kind has advantageous properties for wound closure. This applies particularly in respect of the linear tensile strength, extensibility, tear-out force and pull-through force of the suture material. The suture material can in particular be used as a knotless or self-fixing suture material. A further advantage relates to the production of the suture material. Thus, cutting the barbs into the suture material in the undrawn state thereof particularly advantageously increases the cutting safety when producing the suture material since the original diameter, i.e., the undrawn and therefore greater diameter, of the suture material is available for cutting the barbs. Since a suture material in the undrawn state is generally still soft, the suture material in the undrawn state can be worked more easily and in particular with less wear on a cutting device. A further advantage is that the barbs can be made to right themselves by subsequent drawing alone, i.e., without aids. Generally, the barbs can be righted synchronously to a subsequent drawing.

As has already been mentioned, the suture material is generally suitable for anchoring in biological tissues, particularly in human and/or animal tissues. The tissues can be, for example, skin, fat, fascia, bones, muscles, organs, nerves, blood vessels, connective tissues, tendons or ligaments. The suture material is preferably used in plastic surgery, preferably for tightening the skin. For example, the suture material is suitable for eyebrow lifts. In addition, however, the suture material is also suitable for other surgical indications, particularly for indications in which the use of conventional suture materials is made difficult on account of steric hindrance. For example, the suture material can be used in laparoscopic interventions, particularly for fixing meshes, for example, hernia meshes, prolapse meshes or urinary incontinence meshes.

A further possible area of use of the suture material is in the formation of anastomoses, in particular vascular or intestinal anastomoses.

The elongate main body preferably has cut surfaces which extend in the longitudinal direction of the suture material. The cut surfaces can be flattened off, preferably substantially plane.

Preferably, the elongate main body has cut surfaces which extend in the longitudinal direction of the suture material and which are longer than cut surfaces of the undersides of the barbs. The cut surfaces extending in the longitudinal direction of the suture material in the main body can have a length that corresponds to at least 1.1 times, preferably at least 1.3 times to 2.5 times, the length of cut surfaces of the undersides of the barbs.

The barbs can in principle be formed in different arrangements on the elongate main body of the suture material. For example, the barbs can have a row arrangement, an offset arrangement, a zigzag arrangement, an overlapping arrangement, an offset and partially overlapping arrangement, a spiral or helical arrangement, an arbitrary arrangement, or combinations of these, in the longitudinal and/or transverse direction, preferably in the longitudinal direction, of the suture material. Preferred is an arrangement in which the barbs are distributed across the entire outer surface of the main body, since in this case the suture material can anchor itself particularly firmly in a surrounding tissue area.

Particularly preferred is a spiral-shaped or helical arrangement of the barbs on the elongate main body of the suture material. Particular emphasis is also given to an offset arrangement of the barbs, where the barbs are partially overlapping one another. Such an arrangement may be produced, for example, by forming barbs with a small angular offset and with small intervals between them on the surgical suture material, preferably by flat cuts into the suture material. In such an arrangement each of two adjacent barbs forms an individual barb having a twin-tip configuration ("double-acting" barb). Such a twin-tip configuration may be primarily advantageous in view to firm and secure anchoring of the suture in biological tissue.

The suture material may have at least one set of barbs, particularly two, three or more sets. A set of barbs is to be understood here as meaning an arrangement of barbs, on the elongate main body, that corresponds in respect of the configuration of the barbs, in particular in respect of the height of the barbs, the length of the barbs, the cutting depth of the barbs, the apex angle, the righting angle, the cutting angle, the orientation of the barbs and/or the shape of the barbs.

The suture material particularly preferably has what is called a bidirectional arrangement of barbs. A bidirectional arrangement of barbs is to be understood here as meaning an arrangement in which the barbs are oriented in two different directions. Seen in the longitudinal direction of the suture material, the barbs for a first suture material portion are preferably formed in the direction of another, second suture material portion and, for the other, second suture material portion, are formed in the direction of the first suture material portion. It is particularly preferable if, as seen in the longitudinal direction of the suture material, the barbs for a first suture material portion are oriented in the direction of the center of the suture material and, for another, second surface portion, are likewise oriented in the direction of the center of the suture material. The length of the suture material portions particularly preferably corresponds to approximately half the suture material length, such that the suture material center forms a kind of center of symmetry. In this way, the surgical suture material can be pulled from one end thereof to approximately the center of the length of the suture material through a biological tissue, without any great resistance and, when a pull is exerted in the opposite direction, the barbs stand upright and in this way anchor or fix the suture material in the tissue, without knots being needed.

Particularly advantageously, the surgical suture material has at least two bidirectional arrangements of barbs on its surface. It is particularly preferable if, in relation to a first bidirectional arrangement of barbs, a second bidirectional arrangement of barbs is formed on the suture material surface at approximately 180 degrees in the circumferential direction and preferably offset in relation to the first bidirectional arrangement (cf. FIGS. 2a and 2b). It is also possible for the surgical suture material to have a total of three bidirectional arrangements of barbs. In this case, it is preferable if in relation to a first bidirectional arrangement of barbs, a second bidirectional arrangement of barbs is formed on the suture material surface at approximately 120 degrees in the circumferential direction and preferably offset in relation to the first bidirectional arrangement, which second bidirectional arrangement of barbs is in turn formed at approximately 120 degrees in the circumferential direction and preferably offset in relation to a third bidirectional arrangement of barbs, such that the third bidirectional arrangement of barbs is likewise formed at approximately 120 degrees in the circumferential direction and preferably offset in relation to the first bidirectional arrangement of barbs (cf. FIGS. 3a and 3b).

The suture material can also have surface areas or surface portions without barbs. The suture material preferably has a surface portion without barbs in the area of the center of the main body. In the longitudinal direction of the suture material, this surface portion can have a length of between 1 and 4 cm, particularly of between 1.5 and 3 cm, preferably a length of ca. 2 cm. In this way, the suture material ends can be placed next to each other to form a loop and can preferably be connected to a surgical needle (cf. FIGS. 4a-4c). The other surface portions of the suture material preferably have a bidirectional arrangement on the main body such that, after formation of the loop, the barbs point in one direction towards the loop. The bidirectional arrangement of the barbs can be based on a spiral-shaped arrangement, or on an arrangement in which the barbs are arranged at 180 degrees in the circumferential direction and preferably offset in relation to one another.

The barbs can in principle be designed in different shapes and geometries. For example, the barbs can be escutcheon-shaped, shield-shaped, scale-shaped, wedge-shaped, thorn-shaped, arrow-shaped, V-shaped and/or W-shaped. The barbs are preferably pointed or tapered at their end protruding from the main body. Furthermore, the barbs may have a multi-tip configuration, in particular a twin-tip configuration. An example for barbs having a twin-tip configuration is the above mentioned W-shaped formation of barbs. Barbs having a twin-tip configuration may in particular be based on two flat cuts into the suture material formed with a small angular offset and in small intervals from each other.

The barbs may have what is called an "apex angle $\alpha$" of between 10 and 70 degrees, in particular of between 15 and 60 degrees. The barbs preferably protrude from the elongate main body of the suture material. The barbs preferably have a "righting angle $\beta$" of between 35 and 75 degrees, particularly of between 45 and 60 degrees, measured from the cut surface of the underside of the barb to the cut surface of the main body. Moreover, the suture material can have a "cut surface angle $\gamma$" of between 160 and 178 degrees, preferably of between 168 and 177 degrees or of between 176 and 179 degrees, measured from the cut surface of the main body to the uncut outer surface of the main body.

Particularly advantageously, the barbs have a strengthened back. A strengthening of the backs of the barbs particularly advantageously increases the resistance of the barbs against kinking, particularly under loading, as a result of which the reliability of the wound repair is again enhanced. Overall, a strengthened formation of the backs of the barbs is of advantage especially when using polymers with a low flexural modulus, for example, poly-para-dioxanone (PDO), Monosyn® (triblock terpolymer of glycolide, trimethylene carbonate and $\epsilon$-caprolactone) or polypropylene. The barbs preferably have a back with a material strengthening, particularly in the form of a material accumulation or material thickening.

Preferably, the suture material has an elongation at break of between 20 and 100%, preferably of between 25 and 50%. In this way, the suture material has clear advantages in terms of strength and extensibility, which is especially advantageous for closing wound regions that are exposed to particularly strong compression loads by adjoining muscle tissue.

The barbs, in particular barbs spaced apart in the longitudinal direction, can have a mutual spacing of between 0.5 and 5 mm, preferably of between 1.0 and 2.0 mm, measured from barb tip to barb tip.

In areas of cut surfaces extending in the longitudinal direction of the suture material, the main body preferably has a diameter of between 0.2 and 2.0 mm, in particular of between 0.25 and 1.0 mm. The diameter of the main body, in areas of cut surfaces extending in the longitudinal direction of the suture material, particularly preferably corresponds substantially to the diameter of other areas of the main body. In this way, the barbs can no longer fully fit into undercuts formed by cuts made in the suture material, thereby resulting in a better hold in biological tissues.

The suture material may have a ratio of barb height to diameter of the suture material of between 1.3 and 0.5, in particular of between 1.1 and 0.6. The ratio of barb cut length to diameter of the suture material is preferably between 2 and 0.4, in particular between 1.5 and 0.6. Moreover, the suture material can have a ratio of barb spacing to diameter of the suture material of between 2 and 25, in particular of between 2 and 8.

The suture material is preferably a monofilament suture material. In particular, the suture material can be a pseudo monofilament. It is possible for the suture material to be a multifilament, in particular multifilament yarn. If the suture material is a multifilament suture material, individual filaments, preferably all of the individual filaments, of the suture material comprise the cut barbs.

The suture material generally has a circular cross section. However, other cross-sectional shapes are likewise conceivable. For example, the suture material can have an oval, triangular, square, trapezoidal, rhomboid, pentagonal, hexagonal, star-shaped or cross-shaped cross section. Such cross-sectional shapes can readily be formed with the aid of suitable extrusion dies, which can be produced specific to the customer with any desired cross-sectional shape.

The suture material may have a non-uniform diameter. In particular the suture material may have a periodically or non-periodically variable diameter. The suture material may be conceived to have axially symmetric, toric and/or oval slubs that are disposed at intervals to one another with intermediate suture material sections of comparatively smaller diameter. In other words, a profiled suture material, formed as an undulating or pulsating suture material, for example, may be preferred. The examples specified in this paragraph are advantageous in that different barb structures may be realized which are beneficial in relation to a respective field of application of the suture material.

The suture material can in principle be produced from all materials suitable for the purpose, in particular polymers. The polymers can be resorbable polymers or non-resorbable polymers or partially resorbable polymers. Examples of polymers that can be used are homopolymers, copolymers, terpolymers or tetrapolymers or the like. Suitable polymers are, for example, block polymers, in particular block copolymers or block terpolymers, or graft polymers. The use of arbitrary or random or alternating copolymers or terpolymers is also possible.

Preferably, the suture material is made from a resorbable polymer from the group including polylactide, polyglycolide, poly-$\epsilon$-caprolactone, poly-para-dioxanone, polytrimethylene carbonate, polyhydroxybutyric acid, mixtures thereof, copolymers thereof and terpolymers thereof. The suture material is particularly preferably made from a resorbable copolymer or terpolymer which comprises at least one monomer from the group including lactide, glycolide, trimethylene carbonate, para-dioxanone and $\epsilon$-caprolactone. For example, the suture material can be made from a terpolymer, preferably a triblock terpolymer, comprising glycolide, trimethylene carbonate and $\epsilon$-caprolactone.

The non-resorbable materials can be polymers, metals, metal alloys or natural fibers, for example, silk or cotton. However, non-resorbable polymers are preferred, particularly from the group including polyolefins, polyesters, polyamides, polyurethanes, mixtures thereof, copolymers thereof and terpolymers thereof. For example, the suture material can be formed from polypropylene, polyethylene terephthalate, a linear and preferably aliphatic polyurethane, polytetrafluoroethylene and/or nylon.

Preferably, the suture material may have an additivation. Preferably, the suture material includes additives selected from the group consisting of biological agents, medical agents, pharmaceutical agents, cells, and/or combinations thereof. Biologically active agents are preferably differentiation factors, growth factors, recruiting factors and/or adhesion factors. Appropriate growth factors may be selected from the group consisting of fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insuline-like growth factors (IGF), hepatocyte growth factor (HGF), interleucin-1 B (IL-1 B), interleucin-8 (IL-8), nerve growth factor (NGF), and combinations thereof. Medical and/or pharmaceutical agents may be antimicrobial agents, in particular antibiotic agents, disinfecting agents, growth-promoting agents, anti-inflammatory agents, analgetic agents and/or odor-controlling agents. Preferred cellular additives may be somatic cells, in particular autologous cells, like fibroblasts, chondrocytes and/or precursor cells, in particular stem cells, for example. A cellular additivation of the suture material is advantageous in that substances produced and secreted by the cells may be an aid in accelerating wound healing, for example. Furthermore, such substances, like collagen and/or hyaluronic acid, for example, may be particularly beneficial in plastic surgery to achieve cosmetically satisfactory results, like a smoothing of wrinkles, for example.

For better penetration through a biological tissue, the suture material can also be tapered or pointed at one end, preferably at both ends.

At least one end of the suture material may be connected to a surgical needle. In the case of the above-described loop-shaped suture material, both ends of the suture material are generally connected to a surgical needle. If, by contrast, the suture material has a bidirectional arrangement, it is preferable if both ends of the suture material are each connected to a surgical needle. For connecting the suture material to a surgical needle, the thread is generally inserted into a hole provided for this purpose in the needle, and the needle is then pressed together in the area of the hole.

To avoid bleeding from the incision channel, provision is made for the suture material to have a smaller diameter in the area of its ends than in the other areas of the suture material. In other words, the ends of the suture material can have a tapered diameter. Such a suture material can particularly advantageously be combined with a surgical needle that is itself designed for smaller suture material diameters. In this way, it is possible for the suture material diameter to be approximated to the needle diameter. A diameter ratio of needle to suture material of <2:1, preferably 1:1, is provided. In this way, the incision channel formed by the needle can be better filled by the suture material areas with the original (not tapered) diameter. For tapering of the diameter, the suture material can be peeled away in the area of its ends. This is preferably done by thermal methods or laser techniques. The transition from the original diameter of the suture material to the tapered diameter in the area of the ends of the suture material can be abrupt or continuous, particularly in the form of a gradient. The extrusion technique is particularly suitable for forming a gradual transition. Thus, the draw-off speed during extrusion of a suture material fiber can be varied, in particular periodically varied. This can be done, for example, by modulating the speed of rotation of the roller responsible for drawing off the suture material fiber. Alternatively, additional rollers can be interposed between the extrusion die and the drawoff roller.

We also provide an undrawn surgical suture material with an elongate main body and with barbs for anchoring in biological tissues, particularly in human and/or animal tissues. For further features and details, particularly regarding the elongate body and the barbs, and also regarding other properties of the suture material, reference is explicitly made where possible to the preceding description.

We further provide a surgical kit or set comprising at least one surgical needle and the suture material. For further features and details regarding the kit or set, reference is made to the preceding description.

Moreover, we also provide a method for producing the surgical suture material, comprising the steps of:
  a) cutting barbs into an undrawn suture material fiber, and
  b) drawing the suture material fiber to form the surgical suture material.

In other words, the method is characterized in that first barbs are cut into an undrawn suture material fiber and subsequently the suture material fiber having barbs cut into the fiber is subject to drawing.

Preferably, the barbs are cut in while the undrawn suture material fiber is rotated. The undrawn suture material fiber may be twisted prior to cutting in barbs and untwisted again after the barbs have been cut in. A further option may be that the cut in, undrawn suture material fiber is twisted simultaneously during drawing. The examples specified in this paragraph are advantageous in that a radial, in particular spiral-shaped or helical, arrangement of barbs on the suture material fiber may be produced. Such an arrangement of the barbs may result in a particularly secure fixation of the suture material in biological tissue.

The suture material fiber used is preferably a monofilament. However, the use of a pseudo monofilament is in principle also possible.

Preferably, the barbs are cut into the undrawn suture material fiber with a cutting depth of between 5 and 50%, preferably of between 15 and 45%, particularly of between 20 and 35%, relative to the diameter of the undrawn suture material fiber.

The barbs can also be cut into the undrawn suture material fiber at a cutting angle $\theta$ of between 15 and 50 degrees, preferably of between 20 and 40 degrees, relative to the outer surface of the undrawn suture material fiber. It was surprisingly found that barbs produced by small cutting angles $\theta$ could be made to right themselves, by subsequent drawing of the suture material, more easily than barbs produced by large cutting angles $\theta$. In particular with small cutting angles $\theta$, the difference between righting angle $\beta$ and cutting angle $\theta$ ($\beta-\theta$) is greater than at large cutting angles $\theta$. It was also found that barbs produced by greater cutting angles $\theta$, in particular by cutting angles $\theta \geq 30$ degrees, have greatly strengthened barb backs. In other words, it is possible, through the choice of cutting angle $\theta$, to influence the barb geometry and to produce an optimal barb geometry for the particular use.

Particularly suitably, the barbs are cut into the undrawn suture material fiber thermally, preferably in a temperature range of between 20 and 100° C., in particular of between 30 and 60° C., above the melting point of the suture material fiber.

Compared to purely mechanical cutting, which is also possible, the thermal cutting of the suture material fiber has the advantage that the ends of the cuts produced by thermal cutting in the main body of the fiber are less tapered, in particular less pointed, than in the case of purely mechanical cutting. In this way, the risk of continued tearing of the fiber, starting from the respective ends of the cut, is additionally minimized during drawing of the suture material fiber and also upon loading of the finished suture material.

Preferably, the barbs are cut into the undrawn suture material fiber by a cutting wire suitable for this purpose, in particular a metal wire. A heated, in particular electrically heated cutting wire is preferably used. The cutting wire can, in particular, be a fine wire. A cutting wire with a diameter of between 20 and 50 µm is preferably used. As an alternative to an individual cutting wire, it is also possible to use a group of cutting wires. It is likewise possible to use a metal lattice.

A suitable alternative entails laser cutting methods. In other words, the barbs can also be cut into the undrawn suture material fiber by a laser. Lasers that can be used are, in principle, gas lasers, for example, $CO_2$ lasers, and also solid-state lasers, for example, Nd:YAG lasers. A suitable laser cutting machine generally comprises a laser beam source, a beam guide, and an at least movable focusing lens (concave mirror or positive lens). The beam leaving the beam source is either guided by fiber-optic cables, for example, in a Nd:YAG laser, or by a deflecting mirror, for example, in a $CO_2$ laser, to the machining lens which focuses the laser beam and in this way generates the power densities needed for the cutting, generally in the range of $10^6$ to $10^9$ watt/cm$^2$. Corresponding laser cutting methods are sufficiently known, such that further details are not provided.

The barbs may be cut into the undrawn suture material fiber mechanically, preferably by at least one cutting blade. Conventional cutting devices, comprising a cutting bed, at least one cutting blade and holding or fixing elements, for example, vices, chucks, holding or clamping jaws, can be used for the suture material that is to be cut. For mechanical cutting of the barbs, it is particularly preferable to use a cutting bed with a groove, wherein the groove is provided to receive the suture material fiber that is to be cut. Depending on the depth of the groove, it is possible, when using at least one cutting blade, to specifically influence the cutting depth with which the barbs are cut into the suture material fiber. This is because the at least one cutting blade is generally designed such that cuts can be made only in the areas of the suture material fiber protruding from the groove. This contributes particularly advantageously to further increasing the safety of the cutting in the method.

After the barbs have been cut, the undrawn suture material fiber is drawn preferably with application of heat, in particular in a temperature range of between 20 and 80° C. above the glass transition temperature of the suture material fiber. Warm water or infrared radiation can be used, for example, to generate a suitable heat for the drawing process. To draw it, the cut suture material fiber is usually guided across a roller system, so-called "drawing frame" in which the rollers can have different speeds of rotation. Generally, each subsequent roller has a higher speed of rotation than the preceding roller of the drawing system. As an alternative to the continuous drawing just described, it is also possible to carry out intermittent drawing. For intermittent drawing, the suture material can be clamped between the clamping jaws of a tensioning device and then drawn. To draw the suture material, a drawing ratio of between 2.5 and 8, in particular of between 3 and 5, is preferably chosen.

After it has been drawn, the suture material can be subjected to various post-treatment steps. For this purpose, the suture material is generally tempered (heat treated) in a vacuum or reduced pressure atmosphere. In this way, the crystallinity of the suture material can be increased and the residual monomer content reduced. A further advantage afforded by post-treatment of the suture material is the reduced susceptibility to shrinkage.

A further aspect is a drawn surgical suture material that is obtained or obtainable by a) cutting barbs into an undrawn suture material fiber, and b) drawing the suture material fiber to form the surgical suture material.

Finally, we provide for use of the suture material as a self-fixing or knotless suture material, particularly for anchoring in biological tissues, particularly in human and/or animal tissues. For further features and details, reference is made to the preceding description.

Further features will become clear from the following description of preferred forms and by reference to the examples and the descriptions of the figures and the drawings. Individual features can be realized either singly or severally in combination.

FIG. 1a is a schematic view of a suture material fiber 10 which is present in the undrawn state and whose main body 12 has been cut to form barbs 14. The cuts are made at a cutting angle θ and with a cutting depth t.

Figures 1B, 1C:
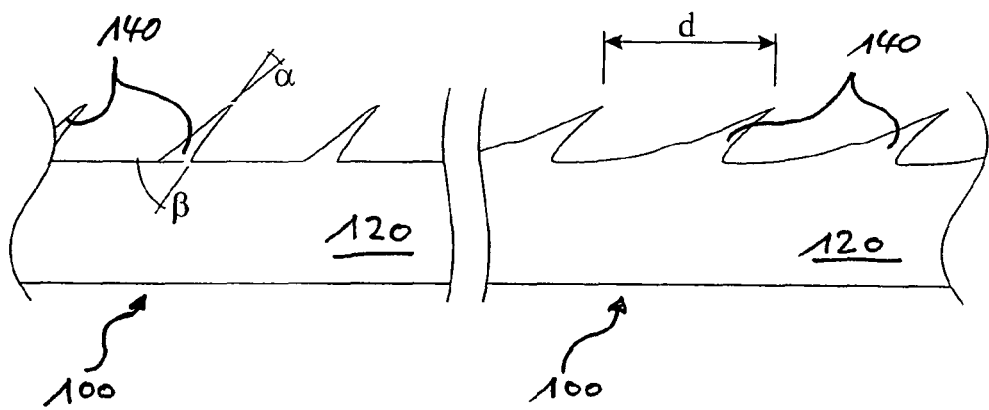
FIG. 1b shows an example of the suture material.
FIG. 1c shows another example of the suture material.

FIG. 1b is a schematic view of a suture material 100 in which cuts are made in the undrawn state to form barbs and which is then drawn. The suture material has an elongate main body 120 from which individual barbs 140 protrude. The barbs 140 are spaced apart from one another by a distance d in the longitudinal direction of the suture material 100. The barbs 140 are arranged such that they are all facing in one direction (unidirectional arrangement). The barbs 140 can be characterized by an apex angle α and by a righting angle β. The apex angle α is to be understood as the angle that results by intersecting an imaginary continuation of the cut surface of the underside of the barb with an imaginary continuation of the back of the barb. The righting angle β represents the angle that is formed by the cut surfaces of the undersides of the barbs and the corresponding cut surfaces of the elongate main body 120. The barbs 140 can have different geometries depending on the chosen cutting angle θ. Barbs 140 produced by cutting angles θ≥30° (cf. FIG. 1c) generally have a much stronger back than barbs 140 produced by smaller cutting angles θ. The strengthened configuration of the backs of the barbs is preferably due to a material strengthening 150 in the form of a material accumulation.

Figure 1D:
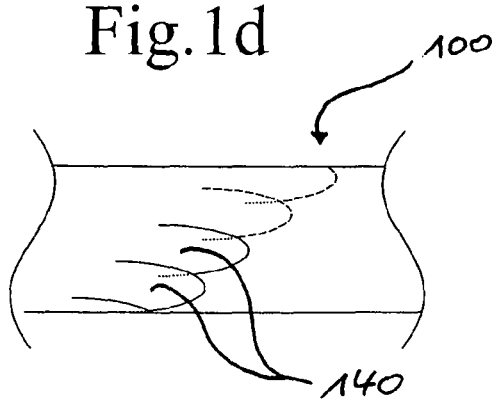
FIG. 1d shows a top view of another example of the suture material.

FIG. 1d is a schematic top view of another example of the suture material 100. The barbs 140 are formed on the surface of the suture material 100 with a small angular offset as well as with small intervals between them. In each case two adjacent barbs 140 together form one barb having a twin-tip configuration ("double-acting" barb). As indicated in FIG. 1d (dashed barb 140), a spiral-shaped or helical type arrangement of the barbs 140 on the surface of the suture material 100 may be produced in this manner.

Figures 2A, 2B:
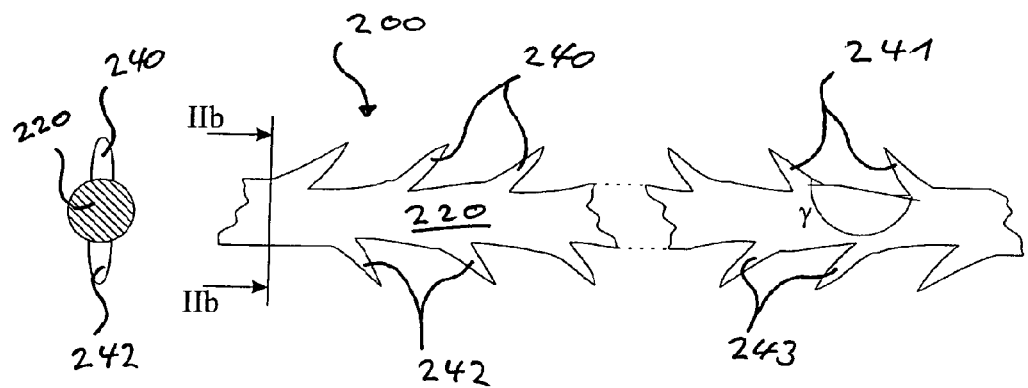
FIG. 2a shows another example of the suture material.
FIG. 2b shows a view of the cross-sectional surface of an example of the suture material.

FIG. 2a is a schematic view of a suture material 200 in which cuts are made in the undrawn state to form barbs 240-243 and which is then drawn, and which has an elongate main body 220 from which the barbs 240-243 protrude. The barbs 240-243 have an offset or staggered bidirectional arrangement on the main body 220. For one half of the suture material, axially spaced apart barbs 240 are arranged at approximately 180 degrees in the circumferential direction and offset in relation to the barbs 242. Similarly, for the other half of the suture material, the barbs 241 are likewise arranged at approximately 180 degrees in the circumferential direction and offset in relation to the barbs 243. The barbs 240 and 241 and the barbs 242 and 243 are each arranged bidirectionally with respect to one another. The suture material 200 can also be characterized by a cut surface angle γ. The cut surface angle γ is to be understood as the angle measured from the cut surfaces of the elongate main body 220 to the uncut outer surface of the elongate main body 220.

FIG. 2b is a schematic view of a cross-sectional surface along an imaginary line IIb-IIb of the example of a suture material described in FIG. 2a.

Figures 3A, 3B:
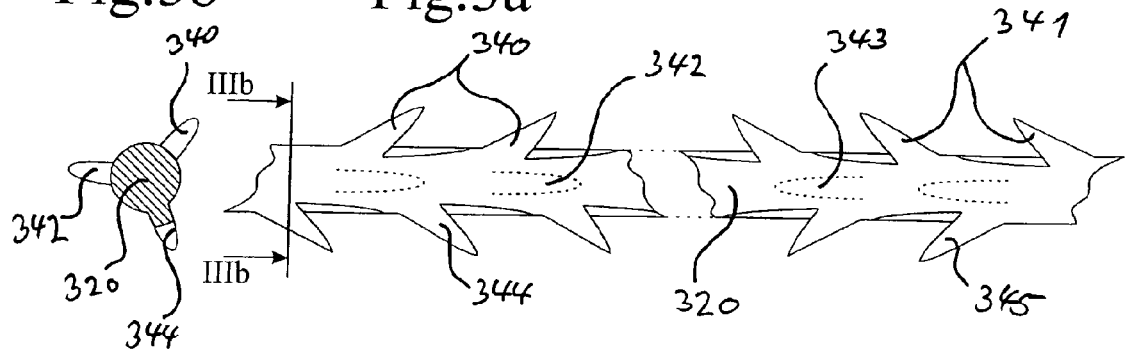
FIG. 3a shows another example of the suture material.
FIG. 3b shows a view of a cross-sectional surface of an example of the suture material.

FIG. 3a is a schematic view of a suture material 300 in which cuts are made in the undrawn state to form barbs 340-345 and which is then drawn, and which has an elongate main body 320 from which the barbs 340-345 protrude. The barbs 340-345 have an offset or staggered bidirectional arrangement on the main body 320. For one half of the suture material, axially spaced apart barbs 340 are arranged at approximately 120 degrees in the circumferential direction and offset in relation to the barbs 342, which in turn are arranged at approximately 120 degrees in the circumferential direction and offset in relation to the axially spaced apart barbs 344. Consequently, the barbs 344 are likewise arranged at approximately 120 degrees in the circumferential direction and offset in relation to the barbs 340. The same applies to the other half of the suture material in respect of the barbs 341, 343 and 345. The barbs 340 and 341, the barbs 342 and 343 and the barbs 344 and 345 are each arranged bidirectionally with respect to one another.

FIG. 3b shows a schematic view of a cross-sectional surface along an imaginary line IIIB-IIIB of the example of a suture material described in FIG. 3a.

Figure 4A:
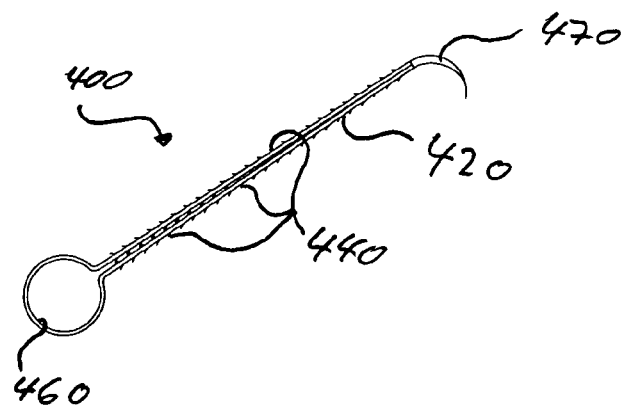
FIG. 4a shows another example of the suture material in combination with a surgical needle.
Figure 4B:
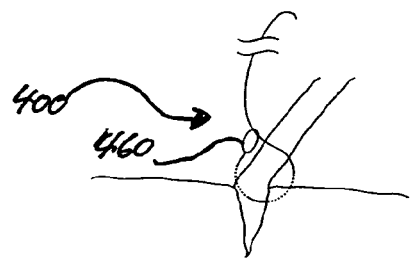
FIGS. 4b and 4c show an operating technique using the combination, shown in FIG. 4a, of a suture material and a surgical needle.
Figure 4C:
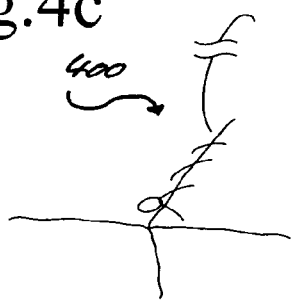

FIG. 4a is a schematic view of a suture material 400 in which cuts are made in the undrawn state to form barbs 440 and which is then drawn and whose ends lie next to each other to form a loop 460 and are connected to a surgical needle 470. There are no barbs in the area of the loop 460, whereas the other areas of the suture material 400 comprise the barbs 440, which protrude from an elongate main body 420. In the drawn state of the suture material 400, the barbs 440 are arranged at approximately 180 degrees in the circumferential direction thereof and offset in relation to one another. After formation of the loop, the barbs 440 point in one direction towards the loop 460. The illustrated combination of surgical suture material 400 and surgical needle 470 is suitable in particular for a knotless wound closure. The loop formation means that a first secure fixation point can advantageously be produced upon closure of a wound, by guiding the suture material 400 through the loop 460 (FIG. 4b). Starting from this first fixation point, a wound is closed using the suture material 400, with the barbs 440 anchoring themselves in the wound area that is to be closed and thereby forming additional fixation points (FIG. 4c). For sake of clarity, the barbs are not shown in FIGS. 4b and 4c.

Figure 5:
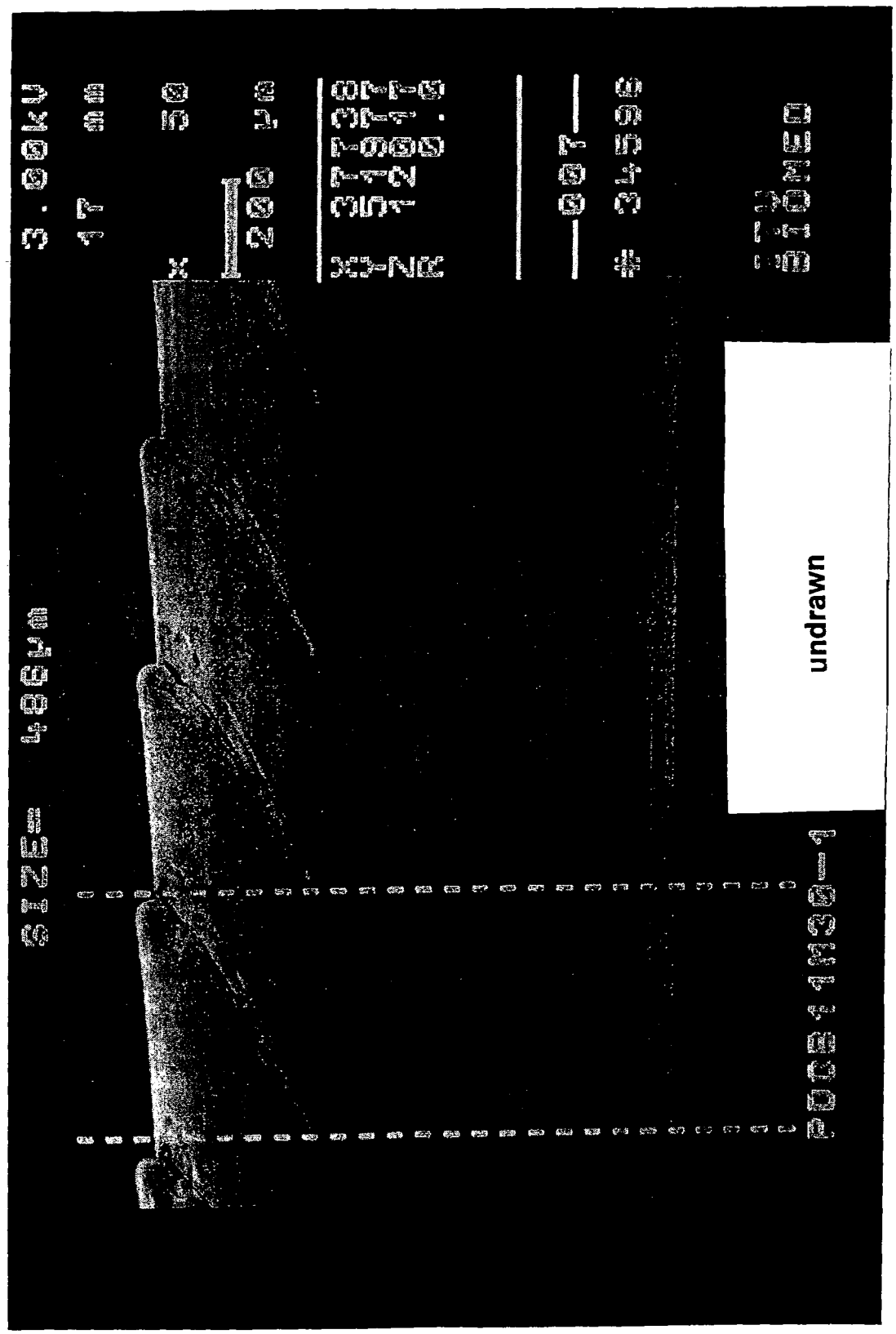
FIG. 5 shows an undrawn PDO filament formed by cutting in barbs.
Figure 6:
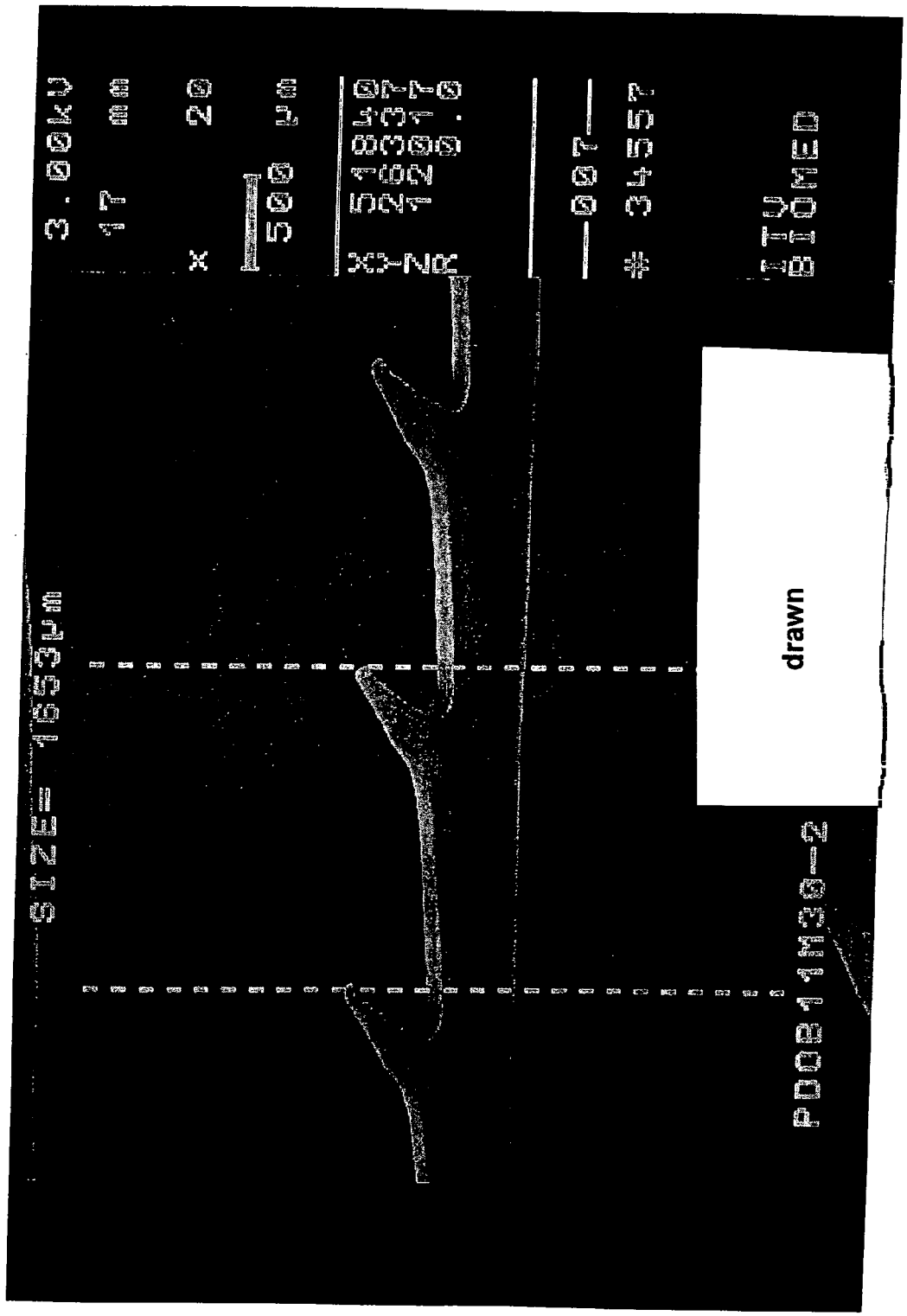
FIG. 6 shows a PDO filament.

FIG. 5 shows a scanning electron micrograph (SEM) of a barbed monofilament made of PDO (poly-para-dioxanone). Herein, the barbs are cut into the PDO monofilament in an undrawn condition. FIG. 6 shows a SEM micrograph of the barbed PDO monofilament subsequent to drawing. Drawing of the cut in, undrawn PDO monofilament effected a marked erection of the barbs relative to the monofilament surface, on the one hand, and formation of back strengthened barbs, on the other hand.

EXAMPLES

Example 1

Producing an Undrawn Poly-Para-Dioxanone Monofilament (PDO Monofilament)

Poly-para-dioxanone (PDO) was dried overnight in a vacuum at ca. 0.3 mbar and at a temperature of ca. 85° C. The extrusion to an undrawn monofilament strand was performed on a Haake TW 100 twin-screw extruder without use of a spinning pump. The spinning head was equipped with a 1.75 mm die with an L/D ratio of 8. The extruder temperature was between 160° C. and 180° C. from the first zone towards the spinning head. The polymer conveyed at a screw speed of 20 rpm built up a die pressure of ca. 120 bar. After leaving the spinning die, the monofilament strand was cooled in a spinning bath of water (room temperature), solidified and then drawn through a roller pair at a speed of 5 m/min and reeled up. The diameter of the undrawn PDO strand was between 1.13 and 1.20 mm.

Example 2

Cutting Barbs into Undrawn PDO Monofilament Pieces

Pieces of an undrawn PDO monofilament that measured ca. 30 cm in length were placed in a 0.8 mm deep and 1.25 mm wide groove of a metal plate and fixed at their ends by clamping devices to generate slight tensioning. The monofilament pieces thus protrude by between 0.33 and 0.40 mm from the groove. A laterally guided metal block ran over the groove on the metal plate and, in the area of the groove, was milled such that it did not graze the part of the monofilament pieces protruding from the groove. The metal block had an oblique plane of optionally 20 degrees, 30 degrees, 40 degrees and 50 degrees with respect to the surface of the metal plate. On this oblique plane, a microtome blade was moved by hand down onto the strand. The cutting depth in the monofilament pieces was predefined by the groove depth and by the diameter of the monofilament pieces. In contrast, the length of the cut varied with the cutting angle θ. After each cut, the block with the oblique plane was moved ca. 0.5 mm on the metal plate in the longitudinal direction of the monofilament pieces before a new cut was made. This procedure was repeated several times.

Example 3

Manual Drawing at Room Temperature

A monofilament piece cut in accordance with Example 2, and undrawn, was removed from the groove of the metal plate and drawn by hand. However, this resulted in the piece breaking in the area of the cuts directly after application of tension, probably as a result of continued tearing starting from the respective ends of the cuts. Repeated tests with cutting angles θ of between 20 and 50 degrees led to the same result.

Example 4

Manual Drawing at Increased Temperature

A PDO monofilament cut in accordance with Example 2, and undrawn, was removed from the groove of the metal plate and drawn manually under hot running water, which was at a temperature of ca. 45° C. In contrast to the drawing described in Example 3, the monofilament piece was able to draw to 4 times its length without tearing. The PDO monofilament pieces with cuts made in them were able to be drawn without any problem independently of the respective cutting angles θ (cutting angle θ of between 20 and 50 degrees). The resulting monofilament diameters were ca. 0.6 mm in relation to areas without barbs. The average spacing between two barbs was between 1.5 and 2.0 mm.

Example 5

Producing a Manually Drawn PDO Monofilament without Barbs, for Comparison Purposes A PDO monofilament strand was produced according to Example 1 and then drawn at room temperature as described in Example 3. The diameter of the monofilament strand was approximately 0.6 mm.

Example 6

Producing Barbs by Cutting a Ready-Drawn PDO Monofilament, for Comparison Purposes To produce barbs in a PDO monofilament that was manually drawn according to Example 5, an automated device was used to make cuts of 0.2 mm in depth at a cutting angle of 25°. The spacing between the cuts was 1.5 mm. Because of the smaller diameter of the drawn monofilament (approximately half the diameter of the undrawn monofilament), the cutting had to be performed with very great care to not cut too deeply into the monofilament.

Example 7

Producing Barbs in a Bidirectional Arrangement, Starting from the Center of Undrawn PDO Monofilament Strands Undrawn PDO monofilament strands were produced according to Example 1 and sectioned to a length of ca. 30 cm. Cuts were then made in the monofilament strands, in the manner described in Example 2, but with the difference that the cuts (with cutting angles $\theta$ of 20 degrees, 30 degrees, 40 degrees and 50 degrees) were made by cutting on both sides from the center of the individual monofilament strands to the strand ends. In this way, the barbs produced pointed from both directions towards the center of the strand, such that the center of the strand formed a center of symmetry. Thereafter, the cut and undrawn PDO monofilament strands were manually drawn, in the manner described in Example 4.

Example 8

Producing Barbs Distributed Across the Outer Surface of PDO Monofilament Strands In the previous examples, the barbs were produced only on that surface of the monofilament strands protruding from the groove and thus lay on a line along the longitudinal axis of the strand. In other words, the previously described examples relate to barbs which are axially spaced apart from one another and which, as has been described in Example 7, may also be present in a bidirectional arrangement. Since a distribution of the barbs across the entire surface of the monofilament strand would in principle be of greater advantage for the hold of the barbs in the tissue, additional tests were carried out to twist undrawn PDO monofilament strands before placement in the groove and only then to make the cuts. To a certain extent, this was also possible with formation of a spiral-shaped arrangement of the barbs. However, in the drawn state, approximately 7 cm were needed for one spiral turn. A higher degree of twisting was not possible without damaging the strand surface and without causing partial drawing by the tension that has to be applied.

Example 9

Producing Barbs Distributed Across the Strand Surface of PDO Monofilament Strands Undrawn PDO monofilament strands that had been sectioned into lengths were cut to produce barbs such that the barbs were distributed across the strand surface. For this purpose, in a first step, four cuts were made at a mutual spacing of 0.5 mm from one another, followed by a gap of 4 mm. In a second step, the strands in the groove of the metal plate were turned through 120° about their longitudinal axis and, beginning in the aforementioned gap of 4 mm in length, were cut in the same sequence. The resulting strands each had 4 mm cuts followed by a 2 mm gap. In a third step, the strand in the groove was turned once again through 120 degrees and, beginning in the first remaining gap of 2 mm in length, were again cut in the above-described sequence. In this way, undrawn strands were obtained in which a group of four barbs was in each case followed by another group of four barbs, which was offset by 120 degrees relative to the preceding group of four on the strand surfaces. After manual drawing carried out according to Example 4, monofilaments were obtained in which the barbs had a substantially spiral-shaped arrangement on the monofilaments, wherein one turn of the spiral took up a length of ca. 2.5 cm and thus represented an improvement on the monofilaments described in Example 8.

Example 10

Producing Barbs in Undrawn PDO Monofilaments by Means of a Thermal Cutting Technique A fine wire with a diameter of ca. 35 µm was clamped into the insulated terminals of a fork-shaped device provided with a handle. The fine wire was then electrically connected to a controllable transformer, such that it could heat up as a function of the applied voltage. In preliminary tests, it was found that a voltage of ca. 5 volts adequately heated the fine wire to melt PDO. An undrawn PDO monofilament strand produced according to Example 1 was placed into a groove of depth 0.8 mm to 0.9 mm in a Teflon plate. The strand was then manually cut into by the electrically heated fine wire. The cuts resulted from a locally restricted melting of the polymer. It was found that very fine cuts could be made in this way. Alternatively to the cutting technique using a heated fine wire, undrawn PDO strands were also able to be easily cut to form barbs by laser beams.

The PDO strands with cuts made in them were then able to be drawn without tearing, as has been described in Example 4.

Example 11

Table Comparing the Barb Geometry Before and After Drawing of a PDO Monofilament in which Cuts were Made in the Undrawn State

TABLE 1

Table comparing the barb geometry before and after drawing

| Undrawn | | Drawn | | | |
|---|---|---|---|---|---|
| Cut surface angle $\theta$ [degrees] | Cutting length s [mm] | Righting angle $\beta$ [degrees] | Height h [mm] | Length l [mm] | Apex angle $\alpha$ [degrees] |
| 20 | 1.02 | 52 | 0.75 | 0.93 | 16 |
| 30 | 0.70 | 54 | 0.48 | 0.59 | 30 |
| 40 | 0.54 | 58 | 0.37 | 0.45 | 42 |
| 50 | 0.46 | 59 | 0.35 | 0.37 | 56 |

Table 1 shows that the barb geometry is dependent on the cutting angle $\theta$. Thus, barbs that were produced with a cutting angle of $\geq 30$ degrees have a significantly smaller barb height and barb length. In addition, barbs with a cutting angle $\theta \geq 30$ degrees generally have a strengthened back, in which respect they differ from barbs that were produced by smaller cutting angles $\theta$.

Example 12

Determining the Linear Tearing Force

The linear tearing force of a PDO monofilament strand drawn manually according to Example 4 was determined and compared to the linear tearing force of a PDO monofilament strand known from the prior art (cuts made in it in the drawn state). The linear tensioning tests were carried out on a Zwick universal testing machine 1435. The clamping length was 200 mm and the test speed 200 mm/min. The results obtained are shown in Table 2.

TABLE 2

Comparison of the linear tearing force and elongation at break between a PDO strand in which cuts were made in the undrawn state, and which was then drawn, and a PDO strand in which cuts were made in the drawn state

| Sample | Maximum tensile force [N] | Elongation at break [%] |
| --- | --- | --- |
| Ex. 4, θ = 20°, hand-drawn | 48.6 | 40.7 |
| Ex. 4, θ = 30°, hand-drawn | 38.4 | 29.6 |
| Ex. 4, θ = 40°, hand-drawn | 35.3 | 26.7 |
| Ex. 4, θ = 50°, hand-drawn | 37.0 | 23.5 |
| Ex. 4, industrially drawn, cut | 33.0 | 15.2 |
| Ex. 5, no barbs, hand-drawn | 76.1 | 103.4 |

The values in Table 2 show that, in terms of strength and extensibility, the PDO strand in which cuts were made in the undrawn state, and which was then drawn, is clearly superior to the conventional PDO strand, i.e., in which cuts are made in the drawn state.

Example 13

Tear-Out Tests for Determining the Efficiency of the Barbs

A cut was made into a ca. 10 mm thick pork cutlet. A PDO monofilament, drawn manually according to Example 4, was then drawn into this cut such that the barb tips were oriented counter to the direction of drawing-in. The monofilament was inserted linearly into the cutlet such that a total of five barbs lay completely within the tissue. After the cutlet had been clamped in a special stationary device of a Zwick tensile testing machine, the monofilament was pulled out of the cutlet in the direction counter to the direction of drawing-in (that is to say in the blocking direction of the barbs) by a mobile clamp of the tensile testing machine. The tear-out force needed to do this was determined. The same test was also carried out with a PDO monofilament strand in which cuts were made in the drawn state. At least six tests were carried out per monofilament, and the mean value was then calculated. The data obtained are shown in Table 3.

TABLE 3

Summary of the tear-out tests

| Sample | Tear-out force [N] |
| --- | --- |
| Ex. 4, θ = 20°, hand-drawn | 1.0 |
| Ex. 4, θ = 30°, hand-drawn | 1.6 |
| Ex. 4, θ = 40°, hand-drawn | 2.1 |
| Ex. 4, θ = 50°, hand-drawn | 2.1 |
| Ex. 6, industrially drawn, cut | 0.9 |

The data in Table 3 show that the tear-out forces increase as the cutting angle θ increases. This was not entirely expected, in view of the dependency of the barb geometry on the cutting angle θ, according to which the barb height and barb length decrease as the cutting angle θ increases. Table 3 also shows that, in the case of our monofilaments, the tear-out forces are greater, for the most part even significantly greater, than for the PDO monofilament known from the prior art (in which cuts were made in the drawn state). Since the tear-out force in turn correlates with the in vivo strength of a "suture," our monofilaments also offer advantages in terms of the safety and load-bearing capacity of wound closures compared to conventional barbed sutures.

Example 14

Determining the Pull-Through Force

In addition to the tear-out force determined in the preceding example, the pull-through force in animal tissue (pork cutlet) was also determined, since the pull-through force is generally a measure of the tissue trauma as a suture material is drawn in. The test set-up corresponded largely to the test set-up described in the preceding example, except that the barbs were drawn into the tissue in a non-blocking manner.

TABLE 4

Summary of the measured pull-through forces

| Sample | Pull-through force [N] |
| --- | --- |
| Ex. 4, θ = 20°, hand-drawn | 0.70 |
| Ex. 4, θ = 30°, hand-drawn | 0.55 |
| Ex. 4, θ = 40°, hand-drawn | 0.65 |
| Ex. 4, θ = 50°, hand-drawn | 0.60 |
| Ex. 6, industrially drawn, cut | 0.50 |

The data in Table 4 show that the pull-through forces measured in our PDO monofilaments were not significantly higher than in a PDO monofilament in which cuts were made in the drawn state.

Overall, our PDO monofilaments are therefore found to have an excellent ratio of tear-out force to pull-through force.

Example 15

Effect of Barb Arrangement

An undrawn PDO monofilament having a diameter of 0.98 mm was cut to a length of 27 cm and fixed in an apparatus to allow rotation of the thread around the longitudinal axis after each cut in. Herein, the angular offset W was arbitrary, and set to a range between 60° (spiral having 6 barbs) and 120° (spiral having 3 barbs). The cutting was performed in a fully automated manner. Each of cutting angle S, cutting depth T, and cutting interval A were adjustable. A test run comprised cutting angles between 20° and 40°, cutting depths between 10% and 30% of the undrawn thread diameter, and cutting intervals between 0.15 and 0.35 mm. After completion of the cutting, the samples were subject to batch-wise drawing in a hot air duct at temperatures between 80° C. and 90° C. In a section free of barbs, a diameter was 0.50±0.02 mm. The drawing ratio was about 4. The samples are tested for linear tensile strength (LTS), linear (LTOF) and radial (RTOF) tear-out force in pork belly with rind, and partially for linear pull-through force (LPTF). Results are listed relative to the state of the art (Quill SRS USP 1) in the following Table 5.

TABLE 5

| Test No. BN | Sample | LTS [N] | Elongation at break (%) | LTOF [N] in pork belly | RTOF [N] in pork belly | LPTF max [N] in pork belly |
|---|---|---|---|---|---|---|
| | Quill SRS USP 1 | 42.6 | 30.9 | 3.9 | 15.0 | 0.3 |
| 81 | S20T25A30W60H VH90 | 35.3 | 35.3 | 6.6 | 17.1 | 0.3 |
| 80 | S20T28A30W60H VH90 | 32.9 | 33.1 | 8.8 | 19.5 | 1.1 |
| 88 | S20T30A50W60H VH85 | 41.1 | 39.0 | 4.1 | 11.7 | — |
| 75 | S20T30A64W120H H90 | 35.9 | 34.0 | 7.6 | 11.9 | 0.2 |
| 86 | S25T30A50W60H VH85 | 43.7 | 49.6 | 5.3 | 9.7 | — |
| 87 | S25T30A50W60H VH85R | 40.0 | 68.9 | 8.7 | 15.5 | — |
| 85 | S25T30A50W120HVH85 | 41.1 | 37.5 | 6.5 | 13.9 | — |
| 76 | S25T30A64W120HVH90 | 35.1 | 31.4 | 5.8 | 12.3 | 0.2 |
| 74 | S30T30A30W60H VH90 | 25.3 | 22.2 | 8.5 | 18.9 | 0.7 |
| 53 | S30T30A30W120HVH90 | 26.5 | 28.6 | 5.0 | 14.5 | 0.6 |
| 83 | S30T30A50W60H VH85 | 39.3 | 36.1 | 6.3 | 13.1 | — |
| 84 | S30T30A50W120HVH85 | 39.9 | 34.2 | 7.4 | 13.3 | — |
| 65 | S30T30A64W60H VH90 | 34.5 | 33.7 | 3.2 | 16.6 | 0.2 |
| 77 | S30T30A64W120HVH90 | 35.3 | 36.5 | 7.2 | 14.8 | 0.3 |
| 44 | S30T30A64W120HVH80 | 32.9 | 31.0 | 3.4 | 16.4 | 0.5 |
| 73 | S30T30A64W120HVH90 | 27.3 | 28.4 | 9.2 | 14.1 | 0.5 |
| 57 | S35T30A30W60H VH90 | 31.4 | 28.6 | 4.1 | 18.5 | 0.3 |
| 55 | S35T30A45W120HVH90 | 27.7 | 25.1 | 4.7 | 14.4 | 0.2 |
| 78 | S35T30A64W120HVH90 | 33.4 | 32.9 | 6.2 | 19.2 | 0.2 |
| 50-1 | S40T30A64W120HVH90 | 33.6 | 27.3 | 3.5 | 16.8 | 0.4 |
| 79 | S40T30A64W120HVH90 | — | — | 4.0 | 13.3 | 0.5 |

A64 = 0.35 mm cutting interval undrawn
A50 = 0.27 mm cutting interval undrawn
A45 = 0.25 mm cutting interval undrawn
A30 = 0.16 mm cutting interval undrawn

The invention claimed is:

1. A method of producing a surgical suture material comprising:
    a) cutting barbs for anchoring in biological tissue into an elongate body of undrawn suture material fiber, and
    b) drawing the suture material fiber to form the surgical suture material.

2. The method according to claim 1, wherein the suture material fiber is twisted before the barbs are cut and is untwisted again after the barbs have been cut.

3. The method according to claim 1, wherein the barbs are cut with a cutting depth of 5 to 50% mm relative to a diameter of the undrawn suture material fiber.

4. The method according to claim 1, wherein the barbs are cut at a cutting angle θ of 15 to 50 degrees relative to an outer surface of the undrawn suture material fiber.

5. The method according to claim 1, wherein the barbs are thermally cut at a temperature of 20 to 100° C. above the melting point of the suture material fiber.

6. The method according to claim 1, wherein the barbs are cut by a cutting wire.

7. The method according to claim 1, wherein the barbs are cut by a laser.

8. The method according to claim 1, wherein the barbs are mechanically cut by at least one cutting blade.

9. The method according to claim 1, wherein the suture material fiber is drawn with application of heat at a temperature of 20 to 80° C. above the glass transition temperature of the suture material fiber.

10. The method according to claim 1, wherein the suture material fiber is drawn at a drawing ratio of 2.5 to 8.

* * * * *